United States Patent
Katagiri et al.

(10) Patent No.: US 6,633,035 B1
(45) Date of Patent: Oct. 14, 2003

(54) WATER CONTENT-MEASUREMENT METHOD AND WATER CONTENT-MEASUREMENT APPARATUS, AND ELECTRICAL COMPONENT-FABRICATION METHOD USING THE MEASUREMENT APPARATUS AND METHOD

(75) Inventors: Junichi Katagiri, Naka (JP); Yoshitaka Takezawa, Hitachinaka (JP); Yuzo Ito, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/831,111
(22) PCT Filed: Oct. 27, 1999
(86) PCT No.: PCT/JP99/05954
§ 371 (c)(1),
(2), (4) Date: May 4, 2001
(87) PCT Pub. No.: WO00/28303
PCT Pub. Date: May 18, 2000

(51) Int. Cl.⁷ ............................................. G01N 21/35
(52) U.S. Cl. .................. 250/339.1; 250/339.11; 250/341.8; 250/341.7
(58) Field of Search .................. 250/339.1, 339.11, 250/341.7, 341.8

(56) References Cited

U.S. PATENT DOCUMENTS

| | | | | |
|---|---|---|---|---|
| 4,463,261 A | * | 7/1984 | Bowman | 250/339.1 |
| 5,131,167 A | * | 7/1992 | Bachmann et al. | 34/246 |
| 5,343,045 A | * | 8/1994 | Gupta | 250/339.1 |
| 5,357,441 A | * | 10/1994 | Petty et al. | 702/104 |
| 6,061,139 A | * | 5/2000 | Takezawa et al. | 356/407 |
| 6,281,500 B1 | * | 8/2001 | Gaon | 250/339.1 |
| 6,459,083 B1 | * | 10/2002 | Finkele et al. | 250/339.11 |

FOREIGN PATENT DOCUMENTS

| | | | |
|---|---|---|---|
| EP | 0 832 730 A2 | 4/1998 | |
| EP | 99 95 1105 | 7/2002 | |
| GB | 2 110 819 A | 6/1983 | |
| GB | 2110819 A | * 6/1983 | G01N/21/31 |

* cited by examiner

Primary Examiner—Albert Gagliardi
(74) Attorney, Agent, or Firm—Antonelli, Terry, Stout & Kraus, LLP

(57) ABSTRACT

A measurement method and apparatus, which are capable of simply measuring the water content of an object with a high degree of accuracy, is characterized by irradiating the surface of the object with at least two monochromatic light beams having different wave length values, one of the wave length values being less than 1350 nm; measuring the intensity of light for each of the light beams reflected from the surface of the object using a light intensity-measurement unit; obtaining the reflective absorbance ($A_\lambda$) of each light beam; calculating a reflective-absorbance differences ($\Delta A_\lambda$) between, or a reflective-absorbance ratio ($A_\lambda'$) of, the respective light beams, respectively; and estimating the water content of the measured object by using the relationship between water content and the reflective-absorbance differences or reflective-absorbance ratio, which relationship stored in a memory device in advance.

5 Claims, 6 Drawing Sheets

WATER CONTENT-MEASUREMENT METHOD AND WATER CONTENT-MEASUREMENT APPARATUS, AND ELECTRICAL COMPONENT-FABRICATION METHOD USING THE MEASUREMENT APPARATUS AND METHOD

TECHNICAL FIELD OF THE INVENTION

The present invention relates to a water content-measurement method and a water content-measurement apparatus for measuring the water content of an object to be measured, such as a paper, a film, etc., using light, and to an electrical component-fabrication method using the measurement.method or the measurement apparatus.

BACKGROUND OF THE INVENTIONS

Concerning a technique for measuring the water content of an object to be measured, there is a two-color infrared water content-measurement device, using absorbed light of 1.94 μm wave length and reference light of 1.7 or 1.8 μm wave length, for obtaining a measure of the water content based on the ratio of two absorption degree signals of the absorbed light and the reference light. Further, for example, Japanese Patent Application Laid-Open Hei 5-164690 discloses a three-color water content-measurement device, which is not affected by the type of object to be measured, or the humidity in the air, by using absorption light of 1.96 and 2.0 μm wave lengths, and reference light of 1.9 and 2.1 μm wave lengths. Also, for example, Japanese Patent Application Laid-Open Sho 60-93334 discloses a water content-measurement method suitable for measurement of high water content, which uses measurement light of 1.76–1.87 μm wave length, and reference light of 1.7 μm wave length.

SUMMARY OF THE INVENTION

However, in the conventional water content-measurement method and apparatus as described above, since an output measurement signal indicating water content deviates due to even a small difference between wave length values 1.7 and 1.8 μm, a high measurement accuracy cannot be realized. Further, the size of the measurement apparatus becomes large because monochromatic light is obtained from continuous spectrum light via a spectrograph or a filter.

Moreover, in the fabrication of electrical components such as transformers, motors, etc., since an insulating paper covering a coil conductor absorbs moisture during insulation paper-covering operations or electrical component-assembling operations, a dry process is performed after the assembling is finished. However, since there has not been a portable water content-measurement device, a problem results in that it is difficult to heuristically dry insulation paper, etc., in just proportions, that is, needless time is consumed by overabundant dry-processing, or the insulation performance of the insulating papers is deteriorated by the shortage in drying the insulating papers due to improperly shortened dry-processing.

An object of the present invention is to provide a water content-measurement method and a water content-measurement apparatus which is capable of measuring the water content of an object be measured, with a high degree of accuracy.

Another object of the present invention is to provide a water content-measurement method which uses a water content-measurement apparatus of reduced size, and which can be compactly composed.

Further, another object of the present invention is to provide an electrical component-fabrication method which is capable of efficiently fabricating an electrical component having excellent insulation characteristics.

From results of examining the relationship between water content and reflectance spectroscopic characteristics of an object to be measured, it has been found that the water content of an object to be measured can be calculated from a change in the reflective-absorbance difference between, or a reflective-absorbance ratio of light beams of two specific wave length values.

The present invention provides a water content-measurement method in which the surface of an object to be measured is irradiated with a light beam having a wave length at which reflective absorbance is largely affected by water content, and a light beam of another wave length at which reflective absorbance is hardly affected by water content, and the reflective absorbance of each light beam is obtained by measuring the intensity of reflected light in each light beam. The method comprises the steps of: irradiating the surface of the object to be measured, with at least two kinds of monochromatic light beams of different wave length values, one of the wave length values being less than 1350 nm, the light beams being directed to the surface of the objective member by a light-guiding device for light-irradiation; measuring the intensity of reflected light in each of the light beams, which light is reflecting from the surface of the object, by directing the reflected light to a light intensity-measurement unit, using a light-guiding device for light reception; obtaining the reflective absorbance ($A_\lambda$) of each light beam, using the equation (1); calculating a reflective-absorbance difference ($A_\lambda$) between, or a reflective-absorbance ratio ($A_\lambda'$) of, the respective light beams, using the equation (2) or the equation (3), respectively; and estimating the water content of the measured object by using the calculated reflective-absorbance difference ($\Delta A_\lambda$) or the calculated reflective-absorbance ratio ($A_\lambda'$), and the relationship between water content, and reflective-absorbance differences ($\Delta A_\lambda$) or reflective-absorbance ratios ($A_\lambda'$), the relationship being stored in a memory device in advance.

$$\text{Here, } A_\lambda = -\log(I_\lambda / I_{0,\lambda}) \qquad (1),$$

$$\Delta A_\lambda = A_{\lambda 1} - A_{\lambda 2} \; (\lambda 1 > \lambda 2) \qquad (2), \text{ and}$$

$$A_\lambda' = A_{\lambda 1} / A_{\lambda 2} \; (\lambda 1 > \lambda 2) \qquad (3),$$

where I: the intensity of light reflecting from the surface of a standard white board, $I_0$: the intensity of the light reflecting from the surface of the measured object, and $\lambda_2$: a wave length value less than 1350 nm.

Further, the present invention provides a water content-measurement apparatus for measuring water content by irradiating the surface of an object to be measured with a light beam having a wave length at which reflective absorbance is largely affected by water content, and a light beam of another wave length at which reflective absorbance is hardly affected by water content. The reflective absorbance of each light beam based on a measured intensity value of reflected light in each light beam. The apparatus comprises: a light source for emitting at least two kinds of monochromatic light beams of different wave lengths, one of the wave length values being less than 1350 nm; a light-guiding device for light-irradiation, for directing the light beams emitted from the light source to the surface of the objective member; a light-guiding device for directing reflected light in each of the light beams, which light is reflecting from the surface of the object; a light intensity-measurement unit for measuring the intensity of light radiated from the light-guiding device; and a calculation and control unit which obtains the reflective absorbance ($A_\lambda$) of each light beam, calculates a reflective-absorbance difference ($\Delta A_\lambda$) between, or a reflective-absorbance ratio ($A_\lambda'$) of, the respective light beams, and estimates the water content of the measured object by using the calculated reflective-absorbance difference ($\Delta A_\lambda$) or the calculated reflective-absorbance ratio ($A_\lambda'$), and the relationship between water content, and reflective-absorbance differences ($\Delta A_\lambda$) or reflective-absorbance ratios ($A_\lambda'$), the relationship being stored in a memory device in advance.

Furthermore, the present invention provides a method of fabricating an electrical component in which a coil conductor covered with an insulating paper is contained in a case, and insulation oil is poured into the case after the coil conductor covered with the insulating paper is dried. The method comprises the steps of: irradiating the surface of the insulating paper with at least two kinds of monochromatic light beams having different wave length values, one of the wave length values being less than 1350 nm, said light beams being directed onto the surface of the insulating paper by a light-guiding device for light-irradiation; measuring the intensity of reflected light in each of the light beams, which light is reflecting from the surface of the insulating paper, by directing the reflected light to a light intensity-measurement unit, using a light-guiding device; obtaining the reflective absorbance ($A_\lambda$) of each light beam, using the equation (1); calculating a reflective-absorbance difference ($\Delta A_\lambda$) between, or a reflective-absorbance ratio ($A_\lambda$) of, the respective light beams, using the equation (2) or (3), respectively; estimating the water content of the measured object member by using the calculated reflective-absorbance difference ($\Delta A_\lambda$) or the calculated reflective-absorbance ratio ($A_\lambda'$), and the relationship between water content, and reflective-absorbance differences ($\Delta A_\lambda$) or reflective-absorbance ratios ($A_\lambda'$), the relationship being stored in a memory device in advance; drying the coil conductor covered with the insulating paper until the water content of the coil conductor becomes less than a predetermined value; and pouring insulation oil into the case.

Here, $A_\lambda = -\log(I_\lambda/I_{0,\lambda})$ (1), $\Delta A_\lambda A_{\lambda 1} - A_\lambda 2$ ($\lambda 1 > \lambda 2$) (2), and $A_\lambda' = A_\lambda 1/A_\lambda 2$ ($\lambda 1 > \lambda 2$) (3), where I: the intensity of light reflecting from the surface of a standard white board, $I_0$: the intensity of light reflecting from the surface of the measured object, and $\lambda_2$: a wave length value less than 1350 nm.

In addition, the present invention provides a method of fabricating an electrical component in which a stator core is wound by a coil conductor covered with an insulating paper, and a varnishing process is performed on the stator core and the coil conductor after the stator core wound by the coil conductor covered with the insulating paper is dried. The method includes the steps of: irradiating the surface of the insulating paper with at least two kinds of monochromatic light beams having different wave lengths, one of the wave length being less than 1350 nm, the light beams being directed onto the surface of the insulating paper by a light-guiding device for light-irradiation; measuring the intensity of reflected light in each of the light beams, which light is reflecting from the surface of the insulating paper, by directing the reflected light to a light intensity-measurement unit, using a light-guiding device; obtaining the reflective absorbance ($A_\lambda$) of each light beam, using the equation (1); calculating a reflective-absorbance difference ($\Delta A_\lambda$) between, or a reflective-absorbance ratio ($A_\lambda'$) of, the respective light beams, using the equation (2) or (3), respectively; estimating the water content of the measured object by using the calculated reflective-absorbance difference ($\Delta A_\lambda'$) or the calculated reflective-absorbance ratio ($A_\lambda'$), and the relationship between water content, and reflective-absorbance differences ($\Delta A_\lambda$) or reflective-absorbance ratios ($A_\lambda$), the relationship being stored in a memory device in advance; drying the coil conductor covered with the insulating paper until the water content of the coil conductor becomes less than a predetermined value; and performing a varnishing process for the stator core and the coil conductor.

Here, $A_\lambda = -\log(I_\lambda/I_{0,\lambda})$ (1), $\Delta A_\lambda A_{\lambda 1} - A_{\lambda 2}$ ($\lambda 1 > \lambda 2$) (2), and $A^{\lambda'} = A_{\lambda 1}/A_{\lambda 2}$ ($\lambda 1 > \lambda 2$) (3), where I: the intensity of light reflecting from the surface of a standard white board, $I_0$: the intensity of light reflecting from the surface of the measured object, and $\lambda_2$: a wave length less than 1350 nm.

Further, concerning the wave lengths of the monochromatic light beams, it is preferable to set $\lambda_1$ in a range of 1400–2000 nm, and B in a range of 600–1350 nm.

Moreover, a semiconductor laser diode or a light emission diode, which emits light having a peak in a wave length range of 600 nm–2000 nm, can be used for the monochromatic light source.

Also, it is preferable to use a glass fiber for the light-guiding device for light-irradiation, and the light-guiding device for light-reception.

BEST MODE FOR CARRYING OUT THE INVENTION

Results of examining the relationship between water content and reflectance spectroscopic characteristics of a measured object shows that the water content of an object to be measured can be calculated from the change in reflective-absorbance difference between, or a reflective-absorbance ratio of, light beams of two specific wave lengths.

Water content is defined as a ratio of the weight of water included in an object to the total weight of the object. That is, by using each measured weight, this water content is obtained from the equation: (the total weight of an object - the weight of water included in the object)/ the total weight of an object.

That is, the water content of an object to be measured can be accurately obtained by the following method comprising the steps of: irradiating the surface of the objective member to be measured, with at least two kinds of monochromatic light beams having different wave lengths, one of the wave lengths being less than 1350 nm, the light beams being directed onto the surface of the object by a light-guiding device for light-irradiation; measuring the intensity of light in each of the light beams, which light is reflecting from the surface of the object, by directing the reflected light to a light intensity-measurement unit, using a light-guiding device; obtaining the reflective absorbance ($A_\lambda$) of each light beam, using the equation (1); calculating a reflective-absorbance difference ($\Delta A_\lambda$) between, or a reflective-absorbance ratio ($A_\lambda'$) of, the respective light beams, using the equation (2) or (3), respectively; and estimating the water content of the measured object member by using the calculated reflective-absorbance difference ($\Delta A_\lambda$) or the calculated reflective-absorbance ratio ($A_\lambda'$), and the relationship between water content, and reflective-absorbance differences ($\Delta A_\lambda$) or reflective-absorbance ratios ($A_\lambda'$), the relationship being stored in a memory device in advance.

Here, $A_\lambda = -\log (I_\lambda / I_{0,\lambda})$ (1), $\Delta A_\lambda A_{\lambda 1} - A_\lambda 2$ ($\lambda 1 > \lambda 2$) (2), and $A^{\lambda'} = A_{\lambda 1}/A_{\lambda 2}$ ($\lambda 1 > \lambda 2$) (3), where I: the intensity of light reflecting from the surface of a standard white board, $I_0$: the intensity of light reflecting from the surface of the measured object, and $\lambda_2$: a wave length value less than 1350 nm.

Further, as the wave length values of the respective monochromatic light beams used in accordance with the present invention, it is preferable to use light of 1400–2000 nm wave length in the near infrared region, whose absorbance changes depending on effects of water content, and light of less than 1350 nm wave length, preferably light of 600–1350 wave length in a visual and near infrared region, whose absorbance is scarcely affected by water content.

Figure 4:
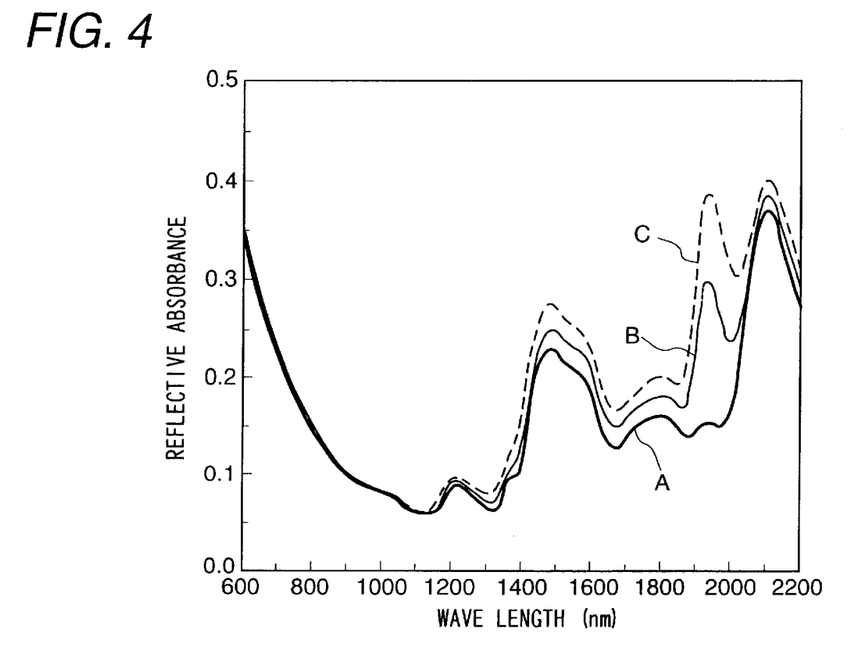
FIG. 4 is a graph showing spectra of light reflecting from insulating papers having different water contents.

The reflective-absorbance spectrum, which reflects a variation in the water content of an object to be measured, changes according to the variation of the water content (A<B<C) as shown in FIG. 4 if craft paper is used for an insulating paper. In the range of less than 1350 wave length, the respective reflective spectra absorbance barely change. However, the height of the peak near 1950 nm wave length in the reflective-absorbance spectrum largely changes as the water content increases, and the reflective absorbance increases in the wide range of 1400–2000 nm wave length in the reflective-absorbance spectrum due to the increase of the water content, which in turn makes it possible to accurately detect the water content.

Moreover, as the monochromatic light source, a semiconductor laser diode (LD) or a light-emission diode (LED), which emits light having a peak in a wave length range of 600–2000 nm, is suitable because these diodes can be easily obtained, and they have a long life time, a stable performance, and a compact size. Specifically, an LD or an LED, which emits light having a peak at 660, 650, 660, 670, 695, 700, 770, 785, 820, 830, 870, 880, 940, 950, 1310, 1550 nm, is suitable for the monochromatic light sources.

An object, whose water content is measured by the water content-measurement method and the water content-measurement apparatus according to the present invention, is mainly paper made of vegetable fiber, such as craft paper, sulfite paper, semi-chemical pulp paper, chemiground pulp paper, refiner groundwood pulp paper, etc.; cellulose derivative paper, such as pressboard paper, cyano-ethyled paper, acetyled paper, etc.; a chemical compound added paper such, as an amine paper, a morpholine paper, an activated alumina paper, etc.; a synthetic fiber mixed paper, including hemp, ramie, mulberry fibers, etc.; a sheet or a film made of fiber, such as cotton, sheep wool, rayon, etc; and a synthetic-fiber sheet or film, made of polyamide, polyamide-imide, polyester, polyurethane, polyvinyle, polyacrylate, polyethylene, polyethylene-naphthalate, polyimide, polycarbonate, polyether-imide, polyethylene-terephthalate, polypropylene, acetate, polystyrene, etc. Further, both the water content-measurement method and the water content-measurement apparatus according to the present invention, are useful for measuring the water content of the surface of a molded article made of epoxy, urethane, polystylene, etc, an article of food, a drug or medicine, a cosmetic, etc.

Figure 1:
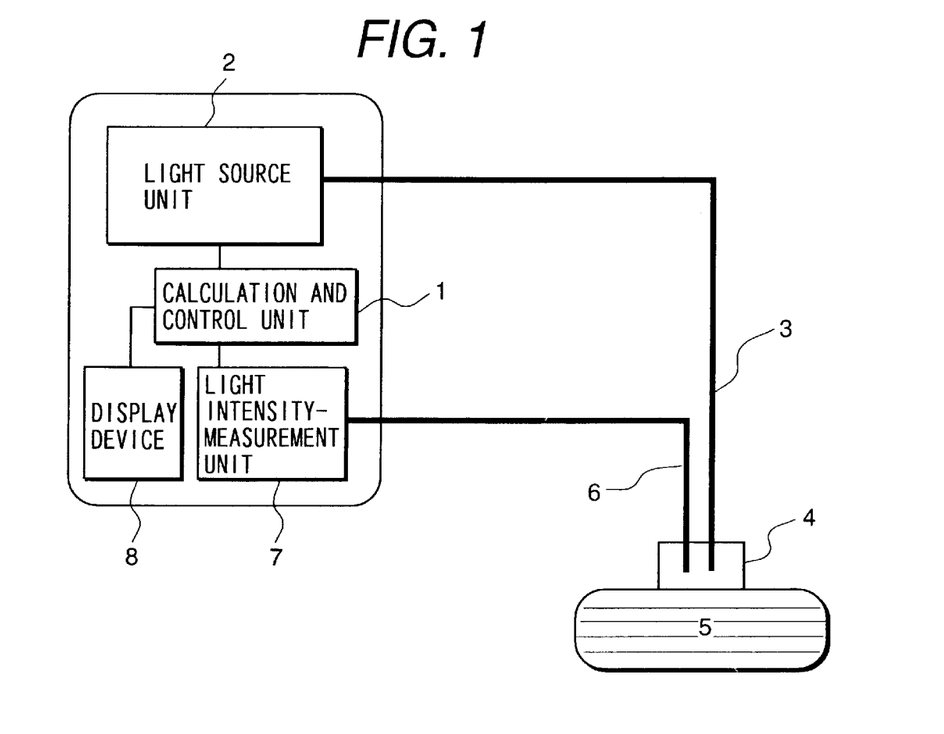
FIG. 1 is a schematic block diagram showing the composition of a water content-measurement apparatus of an embodiment according to the present invention.
Figure 2:
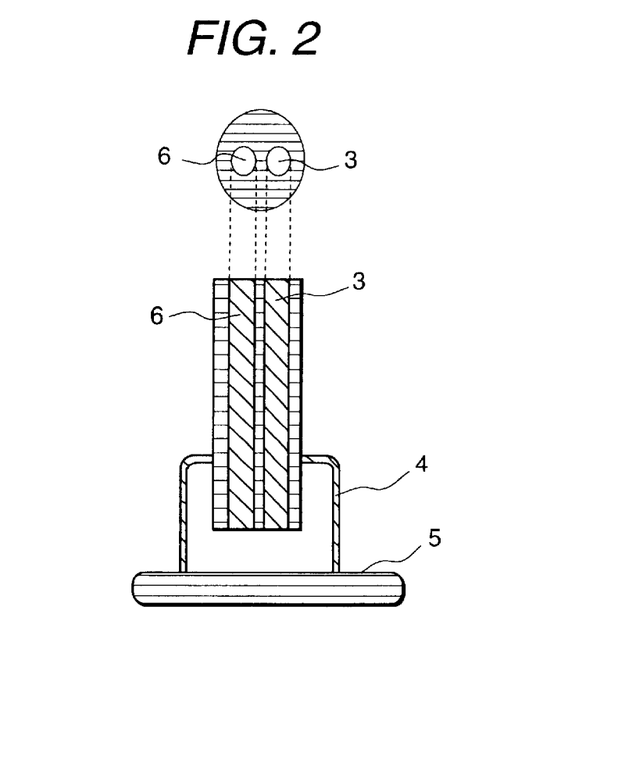
FIG. 2 is a vertical cross section showing the internal structure of a probe in the water content-measurement apparatus shown in FIG. 1.
Figure 3:
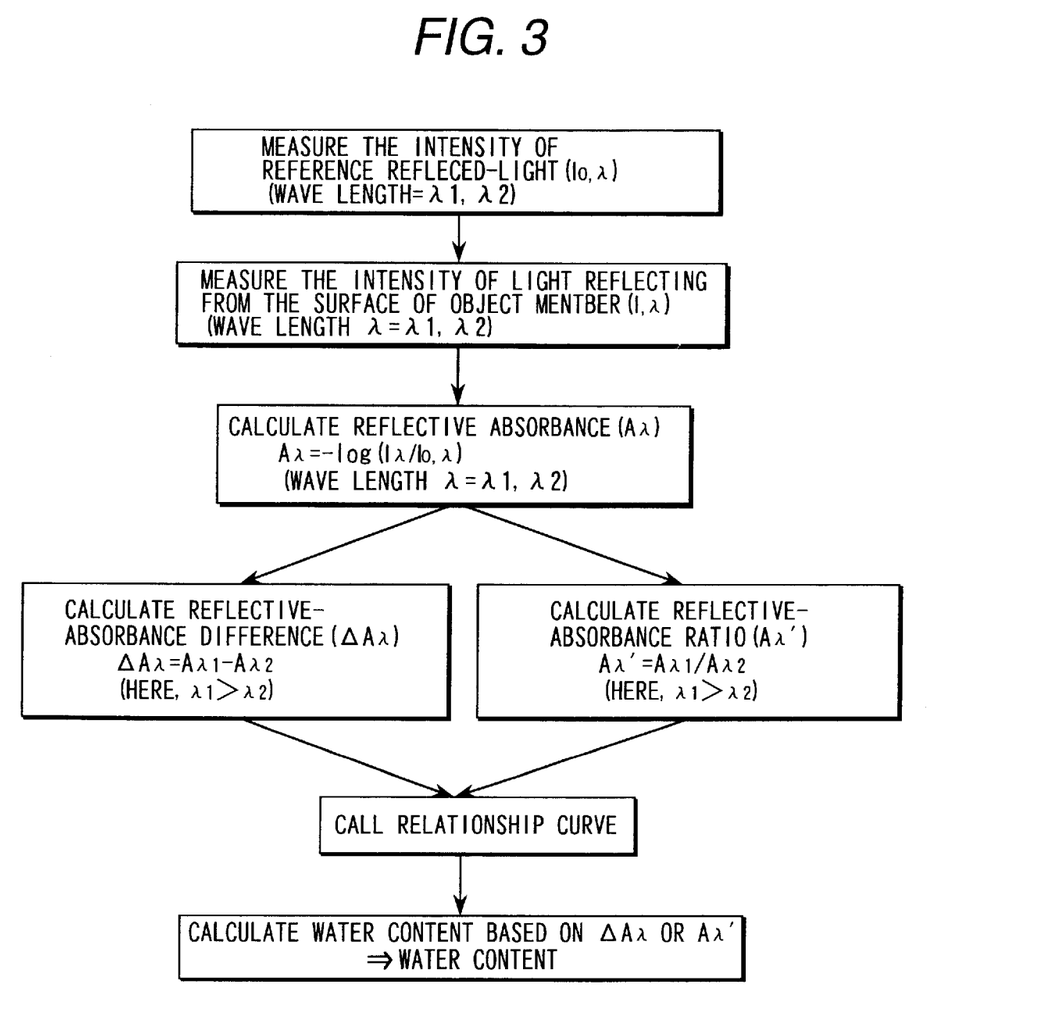
FIG. 3 is a flow chart of the process of calculating water content, which is executed by the water content-measurement apparatus shown in FIG. 1.

FIG. 1 is a schematic block diagram showing the composition of a water content-measurement apparatus representing an embodiment according to the present invention. FIG. 2 is a vertical cross sectional view showing the internal structure of a probe used in the water content-measurement apparatus. Further, FIG. 3 is a flow chart of the process of calculating the water content of an object to be measured.

FIG. 1 and FIG. 2, a calculation and control unit 1 includes a microprocessor in which a memory for storing measured data and a read-on memory are situated, and this calculation and control unit 1 performs control of the switching of the wave length of a light beam emitted from a light source, calculation of the water content, and control of display operations.

A light source unit 2 includes light sources for emitting two monochromatic light beams. For example, an LD for emitting light of $\lambda_1$, (1550 nm) wave length and an LED for emitting light of $\lambda_2$ (950 nm) wave length can be used for the respective light sources.

A light-guiding device for light-irradiation directs a measurement light beam emitted from the light source unit 2 to a probe 4, so as to irradiate an object to be measured using the light beam radiated from the probe 4. Further, a light-guiding device for light reception directs light reflecting from the surface of the object to a light intensity-measurement unit 7. Although plastic fiber, glass fiber, etc., can be used for the light-guiding device for light-irradiation and the light-guiding device for light-reception, glass fiber, whose attenuation factor at the wave length of the light used for the measurement is small, is not suitable.

The light intensity-measurement unit 7 measures the intensity of light reflected from the surface of the object.

A display device 8 is controlled by the calculation and control unit 1, and it displays the measured water content. The calculation and control unit 1 and the display device 8 can be provided by sing a notebook or laptop type personal computer.

In this water content-measurement apparatus, first, in order to obtain a reference level, the reflective absorbance of a measurement light beam of each wave length is measured by putting the probe 4 in contact with a standard white board. That is, a measurement light beam of $\lambda_1$, wave length, which has been generated in the light source unit 2, is transmitted to the probe 4 through the light-guiding device 3, and the standard white board is irradiated with the light beam directed from the probe 4. Further, the light reflecting from the standard white board is directed to the light intensity-measurement unit 7 through the light-guiding device 6. The light intensity-measurement unit 7 detects the intensity ($I_{0,\lambda 1}$) of the reflected light of $\lambda_1$ wave length, and the calculation and control unit 1 stores the value of the detected intensity ($I_{0,\lambda 1}$). Furthermore, in the same manner, the intensity ($I_{0,\lambda 2}$) of the reflected light of $\lambda_2$ wave length is detected, and this detected intensity is stored in the calculation and control unit 1.

Next, the intensity of light reflecting from the object 5 is measured. The probe 4 is put in contact with the surface of the object 5, and the intensity values ($I_{\lambda 1}$, $I_{\lambda 2}$) of the reflected light at the respective wave lengths are detected in the same manner as in the detection of the reference intensify values of the reflected light at the respective wave lengths, which are obtained by using the standard white board, and these values are stored in the calculation and control unit 1. Further, a value of the reflective absorbance of the light beam at each wave length is calculated and stored.

The calculation and control unit 1 calculates the water content of the object based on the relationship between water content and reflective-absorbance differences ($\Delta A_\lambda$), or reflective-absorbance ratios ($A_\lambda'$), which is stored in advance. Further, the result of the calculation is displayed on the display device 8. Here, it is possible to store two groups of relational data expressing the relationship between water content and reflective-absorbance differences ($\Delta A_\lambda$) and the relationship between water content and reflective-absorbance ratios ($A_\lambda'$), and to select one of the two groups, corresponding to the type of object. On the other hand, it is also possible to selectively store one of the two groups in advance, corresponding to the type of object.

The water content-measurement apparatus of this embodiment is composed so that an LD for emitting monochromatic light of $\lambda_1$, wave length and an LED for emitting monochromatic light of $\lambda_2$ wave length are provided in the light source unit 2; each measurement monochromatic light beam of $\lambda_1$ or $\lambda_2$ wave length, which is generated by the LD or the LED, is transmitted to the probe 4 by the light-guiding device 3; the reflected light in the light beam is transmitted to the light intensity-measurement unit 7 by the light-guiding device 6; and the intensity of the reflected light is converted to an electric signal by the light intensity-measurement unit 7. By the above-described arrangement, a portable type water content-measurement apparatus of 5 kg weight can be realized.

EXAMPLE 1 OF MEASUREMENT

The water content of craft paper was measured using the water content-measurement apparatus shown in FIG. 1 and FIG. 2. An LD emitting monochromatic light of $\lambda_1$(=1550 nm) wave length and an LED emitting monochromatic light of $\lambda_2$(=950 nm) wave length, were used in the light source unit 2.

First, after the craft paper of 0.25 mm thickness was dried at 120° C. for 48 hours, the weight of the craft paper was measured, and the craft paper was left at room temperature. Then, the weight of the craft paper was measured again. The water content of the craft paper, which had been left at room temperature, was calculated to be 3.6% from the weight change of the paper.

Next, the water content of the craft paper, which had been left at room temperature, was measured using the water content-measurement apparatus shown in FIG. 1 and FIG. 2, in which monochromatic light of $\lambda_1$(=1550 nm) wave length, emitted by an LD, and monochromatic light of $\lambda_2$(=950 nm) wave length, emitted by an LED, were used. The water content of the craft paper was measured to be 3.7% by the method of measuring water content based on a reflective-absorbance difference, which is indicated in of example 1 of measurement, and the 3.7% water content was displayed on the display device 8. The water content calculated from the weight change was 3.6%, and so a high measurement accuracy was obtained.

EXAMPLE 2 OF MEASUREMENT

The water content of pressboard paper was measured using the water content-measurement apparatus shown in FIG. 1 and FIG. 2. Here, an LD emitting monochromatic light of $\lambda_1$(=1550 nm) wave length and an LD emitting monochromatic light of $\lambda_2$(=830 nm) wave length were used in the light source unit 2. Further, for each of the monochromatic light of 1550 nm wave length and the monochromatic light of 830 nm wave length, the relationship between water content and reflective-absorbance ratios had been input to the calculation and control unit 1 in advance.

First, after the pressboard paper of 0.8 mm thickness was dried at 120° C. for 48 hours, the weight of the craft paper was measured, and the pressboard paper was left in a constant humidity bath. Then, the weight of the craft paper was measured again. The water content of the craft paper, which had been left at room temperature, was calculated to be 13.6% from the weight change of the paper.

Next, the water content of the pressboard paper, which had been left at room temperature, was measured using the water content-measurement apparatus shown in FIG. 1 and FIG. 2, in which monochromatic light of $\lambda_1$(=1550 nm) wave length, emitted by an LD, and monochromatic light of $\lambda_2$(=950 nm) wave length, emitted by an LD, were used. The water content of the craft paper was measured to be 13.5% by the method according to the present invention, and the 13.5% water content was displayed on the display device 8. Thus, the result indicates that a high measurement accuracy was obtained.

EXAMPLE 3 OF MEASUREMENT

The water content of amine paper was measured using the water content-measurement apparatus shown in FIG. 1 and FIG. 2. Here, an LD emitting monochromatic light of $\lambda_1$(=1550 nm) wave length and an LD emitting monochromatic light of $\lambda_2$(=1310 nm) wave length were used in the light source unit 2. Further, for each of the monochromatic light of 1550 nm wave length and the monochromatic light of 1310 nm wave length, the relationship between water content and reflective-absorbance ratios had been stored in the calculation and control unit 1 in advance.

First, after the amine paper of 0.25 mm thickness was dried at 120° C. for 48 hours, the weight of the amine paper was measured, and the amine paper was left at room temperature. Then, the weight of the amine paper was measured again. The water content of the amine paper, which had been left at room temperature, was calculated to be 5.5% from the weight change of the paper.

Next, the water content of the amine paper, which had been left at room temperature, was measured using the water content-measurement apparatus shown in FIG. 1 and FIG. 2., in which monochromatic light of $\lambda_1$(=1550 nm) wave length, emitted by an LD, and monochromatic light of $\lambda_2$(=1310 nm) wave length, emitted by an LD, were used. In this case, the water content of the amine paper was measured to be 5.5% by the method of measuring water content based on a reflective-absorbance difference, and the 5.5% water content was displayed on the display device 8. Thus, this indicates that a high measurement accuracy was obtained.

EXAMPLE 4 OF MEASUREMENT

The water content of an acetate fiber film was measured using the water content-measurement apparatus shown in FIG. 1 and FIG. 2. Here an LD emitting monochromatic light of $\lambda_1$(=1550 nm) wave length and an LD emitting monochromatic light of $\lambda_2$(=635 nm) wave length were used in the light source unit 2. Further, for each of the monochromatic light of 1550 nm wave length and the monochromatic light of 635 mn wave length, the relationship between water content and reflective-absorbance ratios had been stored in the calculation and control unit 1 in advance.

First, after the acetate fiber sheet of 0.5 mm thickness was dried at 120° C. for 48 hours, the weight of the acetate sheet was measured, and the acetate fiber sheet was left at room temperature. Then, the weight of the acetate fiber sheet was measured again. The water content of the acetate fiber sheet which had been left at room temperature, was calculated to be 6.4% from the weight change of the sheet.

Next, the water content of the acetate fiber sheet which had been left at room temperature was measured using monochromatic light of $\lambda_1$(=1550 nm) wave length, emitted by an LD, and monochromatic light of $\lambda_2$(=635 nm) wave length, emitted by an LD. The measured water content of the acetate fiber sheet was 6.5%, which indicates that the high measurement accuracy was obtained.

EXAMPLE 5 OF MEASUREMENT

The water content of polyamide paper was measured using the water content-measurement apparatus shown in FIG. 1 and FIG. 2. Here an LD emitting monochromatic light of $\lambda_1$(=1920 nm) wave length and an LD emitting monochromatic light of $\lambda_2$(=700 nm) wave length, which were obtained from white light via a spectrograph, were used. Further, for each of the monochromatic light of 1920 nm wave length and the monochromatic light of 700 nm wave length, the relationship between water content and reflective-absorbance differences, had been stored in the calculation and control unit 1 in advance.

First, the water content of the polyamide paper of 0.135 mm thickness was calculated to be 6.4% from the weight change of the polyamide paper in the same manner as in the example 1 of measurement.

Next, the water content of the polyamide paper was measured to be 6.6% by the method of measuring water content based on a reflective-absorbance difference, using monochromatic light of $\lambda_1$(=1920 nm) wave length and monochromatic light of $\lambda_2$(=700 nm) wave length, which were obtained from white light via a spectrograph.

EXAMPLE 6 OF MEASUREMENT

The water content of a polyamide film, having a thickness of 0.025 mm, was measured to be 2.8% by the method of measuring water content based on a reflective-absorbance ratio, which was used in the example 1, by using monochromatic light of An (=1400 nm) wave length and monochromatic light of $\lambda_2$(=600 nm) wave length (for each of the monochromatic light of 1400 nm wave length and the monochromatic light of 600 nm wave length, the relationship between water content and reflective-absorbance ratios had been stored in the calculation and control unit 1 in advance). On the other hand, the water content of the polyamide film was calculated to be 2.8% from the weight change of the film.

EXAMPLE 7 OF MEASUREMENT

The water content of sulfite paper, having a thickness of 0.025 mm, was measured to be 7.8% by the method of measuring water content based on a reflective-absorbance ratio, which was used in the example 1, by using monochromatic light of $\lambda_1$(=2000 nm) wave length and monochromatic light of $\lambda_2$ (=1350 ) wave length (for each of the monochromatic light of 2000 nm wave length and the monochromatic light of 1350 wave length, the relationship between water content and reflective-absorbance ratios had been stored in the calculation and control unit 1 in advance). On the other hand, the water content of the sulfite paper was calculated to be 7.9% from the weight change of the paper.

Application example 1 to which the present invention was applied:

The application example 1 will be explained. In this application example, the water content-measurement method according to the present invention is applied to a transformer-fabrication method for fabricating a transformer so as to achieve a high insulation performance by maintaining a predetermined water-content value of an insulating paper used as an insulating member for covering a coil conductor in a high-pressure oil filled transformer, while measuring the water content of the insulating paper in the transformer which has been assembled.

An insulating paper, such as an oil-immersed pressboard paper, has excellent electrical characteristics and is indispensable for use as an insulating member in electrical equipment in which a high voltage is used. However, cellulose fibers, which are a main component of paper, are highly hygroscopic, and, if the paper absorbs moisture, it loses its excellent electrical characteristics. More importantly, it loses the property of an insulating member. Therefore, managing the water content of an insulating paper is extremely important.

Figure 7:
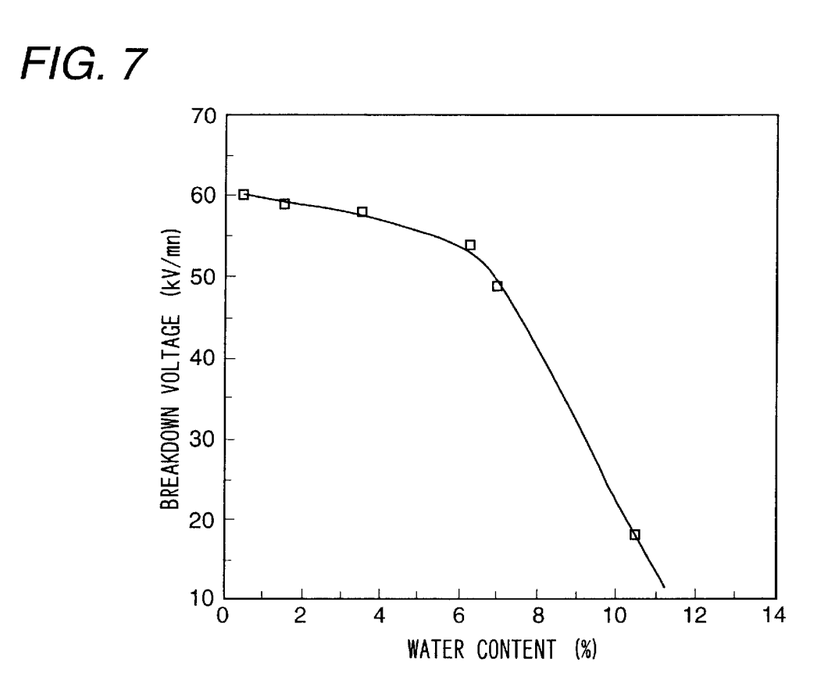
FIG. 7 is a characteristic curve showing the relationship between water content and breakdown voltage.
Figure 8:
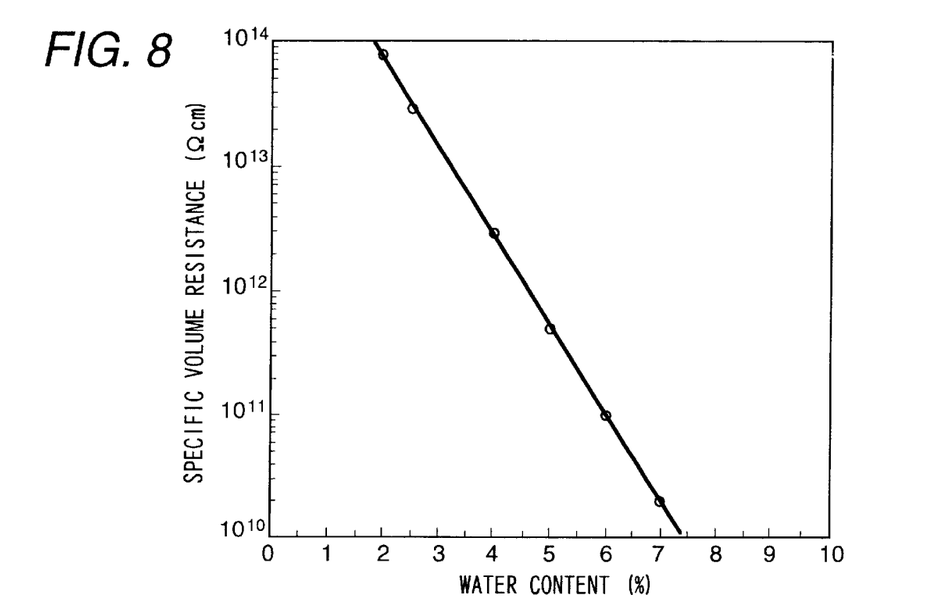
FIG. 8 is a characteristic curve showing the relationship between water content and specific volume resistance.

As shown in FIG. 7 and FIG. 8, the breakdown voltage and the specific volume resistance of an insulating paper, such as pressboard paper, decrease as the water content increases, and this may cause electrical breakdown. Therefore, it is necessary to decrease the water content of the insulating paper by a hot-air drying method or a vacuum drying method.

Figure 9:
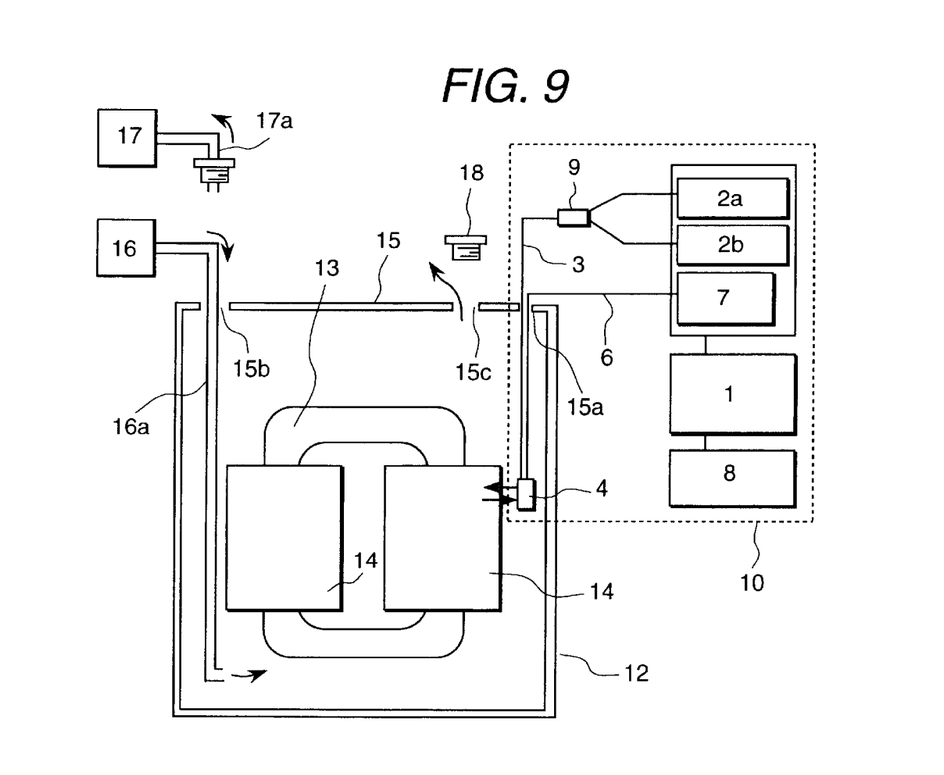
FIG. 9 is a schematic diagram depicting a measurement system for performing an oil filled transformer-fabrication method according to the present invention by using the water content-measurement apparatus of the present invention.
Figure 10:
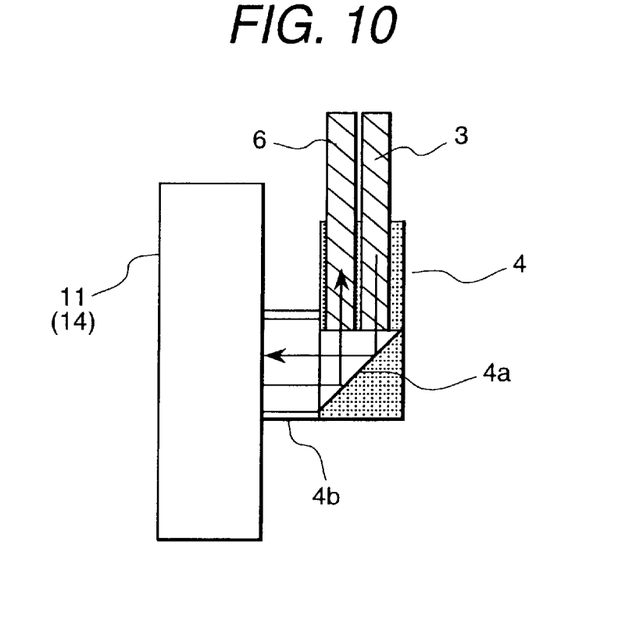
FIG. 10 is a vertical cross section of a probe in the water content-measurement apparatus shown in FIG. 9.

FIG. 9 and FIG. 10 are diagrams for depicting a measurement system which was used to measure the water content of pressboard to be used for insulating a coil of an oil filled transformer of 50 MVA, by using the water content-measurement apparatus shown in FIG. 1 and FIG. 2.

The water content-measurement apparatus 10 directed a measurement light beam emitted from the respective light sources 2a (LD light source emitting light of 1550 nm wave length ($\lambda_1$)) and 2b (LD light source emitting light of 830 nm wave length ($\lambda_2$)) to the light-guiding device 3 for light-irradiation via an optical coupler 9. The probe 4, including a total reflection prism 4a and a stray light-shielding ring 4b, irradiated the object member to be measured (the standard white board 11 or the insulating paper) with the measurement light beam radiated from the light-guiding device 3.

Further, the probe 4 directed the light reflecting from the object into the light-guiding device 6 for light-reception.

In the oil-filled transformer 12, a coil 14, covered by insulation pressboard paper and wound on an iron core 13, was inserted into a case 15. In the case 15 of the oil-filled transformer 12, three holes were formed, including a measurement hole 15a through which the light-guiding device 3 for light-irradiation and the light-guiding device 6 for light-reception were hermetically penetrate in order to place the probe 4 in contact with the surface (the pressboard) of the coil 14; a hot air-introducing hole 15b for introducing hot air ejected from a hot air blower 16 into the bottom space of the case 15; and an air-exhaust hole 15c for exhausting the hot air which has dried the inside of the case 15 and has absorbed moisture.

The top portion of an air-suction pipe 17a connected to a vacuum-drying air-exhaust pump 17 is constructed so that the pump 17 is hermetically connected to the hot air-introducing hole 15c. Further, a tight seal plug 18 for sealing the air-exhaustion hole 15c of the case 15 was provided. Also, the oil-filled transformer 12 was assembled so that the iron core 13, on which the coil 14 was wound, was contained in the case 15.

Under the above conditions, in order to obtain a reference level, the intensity of light, in each of the light beams emitted from each of the light sources 2a and 2b, which is reflected from a standard white board, was measured by putting the probe 4 of the water content-measurement apparatus 10 in contact with a standard white board 11, as seen in FIG. 10. First, the LD light source 2a, emitting a light beam whose wave length $\lambda_1$ was 1550 nm, was turned on, and the intensity ($I_0$, $\lambda_1$) of the light reflecting from the standard white board 11 was measured. This measured intensity of the reflected light was stored in the calculation and control unit 1. Further, the LD light source 2b, emitting a light beam whose wave length $\lambda_2$ was 830 nm, was turned on, and the intensity ($I_0$, $\lambda_2$) of the light reflecting from the standard white board 11 was measured. This measured intensity was also stored in the calculation and control unit 1.

Figure 5:
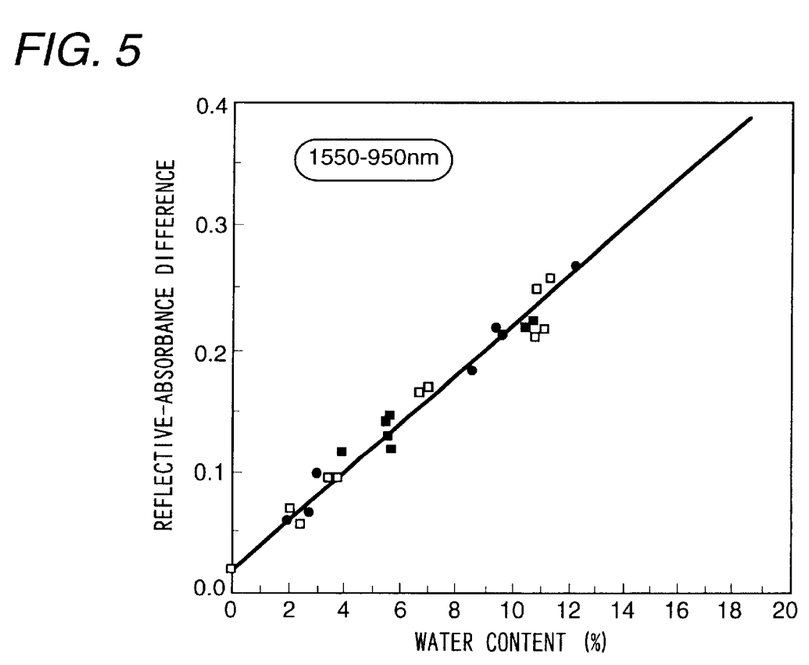
FIG. 5 is a characteristic curve showing the relationship between water content and reflective-absorbance differences.

Next, the light-guiding devices 3 and 6 of the water content-measurement apparatus 10 were passed through the measurement hole 15a of the case 15 of the transformer 12 and connected to the probe 4, which was placed in contact with the pressboard surface of the coil 14. Then, the water content of the surface portion (pressboard paper) of the coil was measured. In the same manner as in the measurement performed on the standard white board 11, the intensity values ($I_{\lambda 1}$, $I_{\lambda 2}$) of two kinds of light reflecting from the surface portion of the coil 14, whose wave length values were $\lambda_1$ and $\lambda_2$, respectively, were measured, and these intensity values were stored in the calculation and control unit 1. Further, the reflective absorbance values ($A_{\lambda 1}$, $A_{\lambda 2}$) of the two kinds of light reflecting from the surface portion of the coil 14, having the respective two wave length values, were calculated. Furthermore, a reflective-absorbance difference ($\Delta A_\lambda$) between the two reflective absorbance values ($A_{\lambda 1}$, $A_{\lambda 2}$) was calculated and stored. Then, the water content was calculated, using the relationship between water content and reflective-absorbance differences ($\Delta A_\lambda$) as shown in FIG. 5. In this example, the calculation result of the water content indicated 8.2%. Moreover, the dry conditions corresponding to the obtained water content, such as the drying time, were obtained, and they were displayed on the display device 8.

During the drying operations, while the dry conditions shown on the display device 8 were referred to, an air-blasting pipe 16a connected to the heating air blower 16 was passed through the hot air-introducing hole 15b, and hot air which had been heated to 110° C. was fed to the bottom space in the case 15, corresponding with the measured water content. The hot air, which was fed to the bottom portion of the case 15, dried the inside of the case 15, while absorbing moisture, and was expelled from the air-exhaust hole 15c to the outside. After the hot-air drying operation was finished, the air-blasting pipe 16a was withdrawn through the hot air-introducing hole 15b, and the air-suction pipe 17a connected to the vacuum-drying air-exhaust pump 17 was connected to the hot air-introducing hole 15b, and the air-exhaust hole 15c was sealed with the tight seal plug 18. Then, the inside of the case IS was vacuum-dried by operating the vacuum-drying air-exhaust pump 17. After the above vacuum-drying was finished, the pressboard paper surface portion of the coil 14 was measured, and the result of the measurement indicated 0.5%.

Then, the light-guiding devices 3 and 6 of the water content-measurement apparatus 10 were withdrawn, and the probe 4 was taken out. Furthermore, the air-suction pipe 17a of the vacuum-drying air-exhaust pump 17 was withdrawn, and the drying operation was finished. The case 15 was then filled with insulation oil. Thus, an oil-filled transformer having excellent insulation-characteristics was fabricated.

APPLICATION EXAMPLE 2 TO WHICH THE PRESENT INVENTION WAS APPLIED

Figure 11:
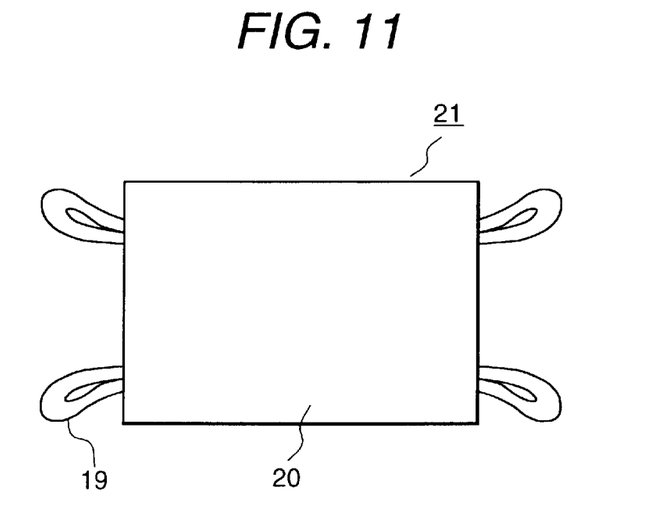
FIG. 11 is a side elevation of a stator fabricated by an electrical component-fabrication method according to the present invention.

Insulation covering processes for covering a stator of a motor with insulation were carried out in the same manner as the above-described processes. The stator of the motor was fabricated by winding a stator coil covered with an insulating paper on a stator core, and the insulation process of impregnating the stator coil and the stator core with insulating varnish was performed after drying. It is desirable that the water content of the insulating paper is maintained at a predetermined value. FIG. 11 schematically shows the composition of a stator 21 of a motor, which is fabricated by winding a stator coil 19 covered with a polyamide insulating paper on a stator core 20.

Figure 6:
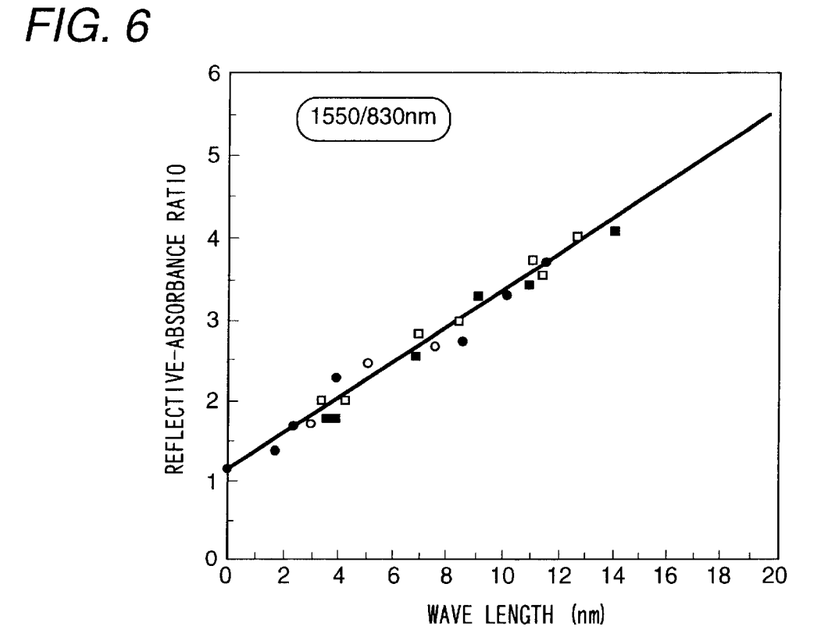
FIG. 6 is a characteristic curve showing the relationship between water content and reflective-absorbance ratios.

By using a water content-measurement apparatus (the illustrating of which is omitted) similar to the measurement apparatus shown in FIG. 11, which was used for the application example 1, in order to obtain a reference level, the intensity of light reflecting from a standard white board, in a light beam emitted from each light source, was first measured by placing a probe of the water content-measurement apparatus in contact with a standard white board 11. Next, the probe 4 was placed in contact with the surface (polyamide paper) of the stator coil 19, and the intensity values ($I_{\lambda 1}$, $I_{\lambda 2}$) of two kinds of light reflecting from the surface of the stator coil, whose wave length values were $\lambda_1$ and $\lambda_2$, respectively, were measured, and these intensity values were stored in the calculation and control unit. Further, the reflective absorbance values ($A_{\lambda 1}$, $A_{\lambda 2}$) of the two kinds of the light reflecting from the surface of the stator coil 19, having the respective two wave length values, were calculated. Furthermore, the reflective-absorbance ratio ($A_\lambda'$) between the two reflective absorbance values was calculated and stored. Then, the water content was calculated, using the relationship between water content and reflective-absorbance ratios ($A_\lambda'$) as shown in FIG. 6. In this example, the calculation result of the water content indicated 7.2%. Moreover, the dry conditions corresponding to the obtained water content, such as the drying time, were obtained, and they were displayed on the display device.

During the drying operations, while the dry conditions shown on the display device 8 were referred to, the stator 21 was placed into an electric oven in which the temperature was kept at 130° C., and the stator 21 was dried. Then, the water content of the surface of the stator was measured to be 0.5%.

After the drying operations were finished, insulation processing was performed for the stator coil 19 by using insulation varnish, and the stator 21 having excellent insulation-characteristics was fabricated.

By the above-described water content-measurement method and apparatus, since the water content of an object can be non-destructively and simply measured, it is possible to efficiently and reliably dry an insulating paper used in a transformer or motor to achieve a proper dry state (water content), while measuring the water content of the object. Further, by filling the casing of a transformer with insulation oil, or performing an insulation process on a motor using insulation varnish, it is possible to fabricate a highly reliable transformer or a motor which has a high breakdown voltage and excellent insulation characteristics.

In accordance with the present invention, the water content of an object, such as paper, a film, etc., can be non-destructively, accurately, and simply measured. Further, it is possible to provide a water content-measurement apparatus which can be portably used. Furthermore, by using such a water content-measurement apparatus, an electrical component having excellent insulation characteristics can be efficiently fabricated.

What is claimed is:

1. A method of fabricating an electrical component in which a coil conductor covered with an insulating paper is contained in a case, and insulation oil is poured into said case after said coil conductor covered with the insulating paper is dried, said method comprising:

irradiating a surface of said insulating paper with at least two kinds of monochromatic light beams of different wave length values λ1 and λ2, one of said wave length values being less than 1350 nm, said light beams being led to said surface of said insulating paper by a light-guiding device for light-irradiation;

measuring an intensity of light in each of the light beams which is reflecting from said surface of said insulating paper by leading said reflected light to a light intensity-measurement unit using a light-guiding device for light-receive;

obtaining reflective absorbance ($A_\lambda$) of each light beam using equation (1);

calculating a reflective-absorbance difference ($\Delta A_\lambda$) between, or a reflective-absorbance ratio ($A_\lambda'$) of, said respective light beams using equation (2) or (3), respectively;

estimating water content of said coil conductor covered with said insulating paper by using said calculated reflective-absorbance difference ($\Delta A_\lambda$) or said calculated reflective-absorbance ratio ($A_\lambda'$), and relationship between water content and reflective-absorbance differences ($\Delta A_\lambda$) or reflective-absorbance ratios ($A_\lambda'$), said relationship being memorized in a memory device in advance;

drying said coil conductor covered with said insulating paper until said water content of said coil conductor becomes less than a predetermined value; and pouring insulation oil into the case;

wherein, $A_\lambda = -\log(I_\lambda/I_{0,\lambda})$ (1)

$\Delta A_\lambda = A_{\lambda,1} - A_{\lambda,2}$ (here, $\lambda 1 > \lambda 2$) (2), and $A_\lambda' = A_{\lambda,1}/A_{\lambda,2}$ (here, $\lambda 1 > \lambda 2$) (3), where I: intensity of light reflecting from a surface of a standard white board, $I_0$: said intensity of said light reflecting from said surface of said measured object member, and $\lambda_2$: a wave length value less than 1350 nm.

2. A method of fabricating an electrical component in which a stator core is wound by a coil conductor covered with a insulating paper, and a varnishing process is performed for said stator core and said coil conductor after said stator core wound by said coil conductor covered with said insulating papers is dried, said method comprising:

irradiating a surface of said insulating paper with at least two kinds of monochromatic light beams of different wave length values λ1 and λ2, one of said wave length values being less than 1350 nm, said light beams being led to said surface of said insulating paper by a light-guiding device for light-irradiation;

measuring an intensity of light in each of the light beams which is reflecting from said surface of said insulating paper by leading said reflected light to a light intensity-measurement unit with a light-guiding device for light-receive;

obtaining reflective absorbance ($A_\lambda$) of each light beam using equation (1);

calculating a reflective-absorbance difference ($\Delta A_\lambda$) between, or a reflective-absorbance ratio ($A_\lambda'$) of, the respective light beams using equation (2) or (3), respectively;

estimating water content of said coil conductor covered with said insulating paper by using said calculated reflective-absorbance difference ($\Delta A_\lambda$) or said calculated reflective-absorbance ratio ($A_\lambda'$), and relationship between water content and reflective-absorbance differences ($\Delta A_\lambda$) or reflective-absorbance ratios ($A_\lambda'$), said relationship being memorized in a memory device in advance;

drying said coil conductor covered with said insulating paper until said water content of said coil conductor becomes less than a predetermined value; and performing a varnishing process for said stator core and said coil conductor;

wherein, $A_\lambda = -\log(I_\lambda/I_{0,\lambda})$ (1), $\Delta A_\lambda = A_{\lambda,1} - A_{\lambda,2}$ (here, $\lambda 1 > \lambda 2$) (2), and $A_\lambda' = A_{\lambda,1}/A_{\lambda,2}$ (here, $\lambda 1 > \lambda 2$) (3), where I: intensity of light reflecting from a surface of a standard white board, $I_0$: said intensity of said light reflecting from said surface of said measured object member, and $\lambda_2$: a wave length value less than 1350 nm.

3. A method of fabricating an electrical component according to one of claim 1 and claim 2, wherein said wave length value λ1 of one of said two kinds of said monochromatic light beams is in a range of 1400–2000 nm, and said wave length value λ2 of another of said two kinds of said monochromatic light beams is in a range of 600–1350 nm.

4. A method of fabricating an electrical component according to one of claim 1 and claim 2, wherein one of a semiconductor laser diode and a light-emitting diode, which has a peak in a range of 600–2000 nm, is used as a light source of each monochromatic light beam.

5. A method of fabricating an electrical component according to one of claims 1 and 2, wherein glass fibers are used for said light-guiding device for light-irradiation and said light-guiding device for light-receive.

* * * * *